United States Patent
Banfield et al.

(10) Patent No.: US 6,764,847 B2
(45) Date of Patent: Jul. 20, 2004

(54) BACTERIAL METHOD FOR CONVERSION OF ARSENITE TO ARSENATE

(75) Inventors: Jillian F. Banfield, Berkeley, CA (US); Thomas M. Gihring, Madison, WI (US); Robert J. Hamers, Madison, WI (US)

(73) Assignee: Wisconsin Alumni Research Foundation, Madison, WI (US)

(*) Notice: Subject to any disclaimer, the term of this patent is extended or adjusted under 35 U.S.C. 154(b) by 0 days.

(21) Appl. No.: 09/828,576

(22) Filed: Mar. 30, 2001

(65) Prior Publication Data

US 2004/0072313 A1 Apr. 15, 2004

(51) Int. Cl.⁷ .................................................. B09B 3/00
(52) U.S. Cl. ............................. 435/262.5; 423/DIG. 17
(58) Field of Search ....................... 435/262.5; 210/668, 210/683; 423/DIG. 17

(56) References Cited

U.S. PATENT DOCUMENTS 5,591,346 A * 1/1997 Etzel et al. .................. 210/668
6,203,709 B1 * 3/2001 Min et al. .................... 210/683

OTHER PUBLICATIONS

Wilkie, J.A. et al., Rapid Oxidation of Geothermal Arsenic (III) in Streamwaters of the Eastern Sierra Nevada; Environ. Sci. Technol. 1998, vol. 32, pp. 657–662.*

* cited by examiner

Primary Examiner—David A. Redding
(74) Attorney, Agent, or Firm—Quarles & Brady LLP

(57) ABSTRACT

A method for converting arsenite in a source to arsenate is disclosed. The method involves incubating bacteria of a Thermus species in the source at a temperature at which the bacteria can convert at least some of the arsenite to arsenate.

11 Claims, 3 Drawing Sheets

US 6,764,847 B2

BACTERIAL METHOD FOR CONVERSION OF ARSENITE TO ARSENATE

STATEMENT REGARDING FEDERALLY SPONSORED RESEARCH OR DEVELOPMENT

This invention was made with United States government support awarded by EPA R826289-01-1. The U.S. Government retains certain rights in this invention.

CROSS-REFERENCE TO RELATED APPLICATIONS

Not applicable.

BACKGROUND OF THE INVENTION

Arsenic is one of the most abundant and widely distributed anthropogenic pollutants in many contaminated sites, and can be a significant source of poisoning in agricultural workers, smelters, miners, and chemical plant workers. Moreover, arsenic poisoning due to contamination of drinking water affects thousands of people worldwide. The common method of removing arsenic from water uses chlorine or ozone, and the waste products from such methods are harmful to people.

The chemistry of arsenic is very complex. While some forms of arsenic become tightly bound to surrounding matter, one of the more toxic forms, arsenite, is also the most mobile. For example, arsenite (AsIII) is more toxic than arsenate (AsV) and arsenite is more mobile in the environment than arsenate. Cullen, W. R., Reimer, K. J. Chem. Rev. 1989, 89, 713–764. In general oxidized forms of arsenic tend to be less mobile in, and easier to remove from, the environment. Thus, it is desirable to convert arsenite to arsenate.

The oxidation of arsenite to arsenate in the absence of catalyst is kinetically inhibited. Wilke and Hering reported that certain microorganisms may be able to catalyze the oxidization of arsenite to arsenate at 25° C. Wilkie, J. A., Hering, J. G. Rapid Oxidation of Geothermal Arsenic (III) in Streamwaters of the Eastern Sierra Nevada, *Environ. Sci. Tehnol.* 1998, 32, 657–662. However, the identity of the microorganisms in Wilke and Hering are not known. Id. Several microorganisms are known to be able to oxidize arsenite. These microorganisms include heterotrophs *Pseudomonas putida* and *Alcaligenes faecalis* as well as the chemolithoautotrophic arsenite-oxidizers *Pseudomonas arsenitoxidans* and "NT-26." Turner., A. W. *Aust. J. Biol. Sci.* 1954, 7, 452–478.; Osborne, F. H., Ehrlich, H. L. *J. Appl. Bacteriol.* 1976, 41, 295–305.; Ilyaletdinov, A. N., Abrashitova, S. A. *Mikrobiologiya* 1981, 50, 197–204; Santini, J. M., Sly, L. I; Schnagl, R. D., Macy, J. M. *Appl. Environ. Microbiol.* 2000, 66, 92–97.

Arsenic is a common constituent of geothermal fluids with typical concentrations of 1–10 mg $L^{-1}$. Ballantyne, J. M., Moore, J. N. *Geochim. Cosmochim. Acta* 1988, 52, 475–483. As a result, levels of arsenic are often elevated in surface waters and aquifiers surrounding hot springs. Welch, A. H., Westjohn, D. B., Helsel, D. R., Wanty, R. B. *Ground Water* 2000, 38, 589–604. For example, at Yellowstone National park, over 100,000 kg of geothermally-derived arsenic is estimated to leave the western boundary each year, affecting water quality within a large region. Nimick, D. A., Moore, J. N. Dalby, C. E., Savka, M. W. *Water Resour. Res.* 1998, 34, 3051–3067. Stauffer, Jenne and Ball reported that rapid arsenite oxidation at high temperature was observed in the drainage of the Azure Hot Spring of Yellowstone but did not explain why. Stauffer, R. E., Jenne, E. A., Ball, J. W. *Chemical Studies of Selected Trace Elements in Hot-Spring Drainages of Yellowstone National Park*, 1980, Geological Survey Professional Paper1044-F.

Thermus species bacteria are Gram-negative aerobic rods found in warm waters such as hot springs, hot water tanks and thermally polluted waters. The Thermus species have been studied extensively in pursuit of novel enzymes and biochemical pathways for industrial applications. Alfredsson, G. A., Kristjansson, J. K. In Thermus species, Sharp, R., Williams, R. Eds., Plenum: New York, 1995; Chapter 2. For example, the Taq enzyme used in polymerase chain reaction was first isolated from *Thermus aquaticus*. So far, no information exists regarding Thermus species' interaction with arsenic-rich fluids.

BRIEF SUMMARY OF THE INVENTION

The present invention is summarized in that bacteria of a Thermus species can be used to convert arsenite to arsenate. An arsenic contaminated source containing arsenite can be detoxified by incubating bacteria of a Thermus species in the source at a temperature and under conditions in which the bacteria can convert at least some of the arsenite to arsenate.

It is an object of the present invention to detoxify arsenic using microorganisms.

It is another object of the present invention to detoxify arsenic with microorganisms at a relatively high temperature.

It is an advantage of the present invention that no harmful products are generated through the arsenic detoxification process.

Further objects, features and advantages of the invention will be apparent from the following detailed description when taken in conjunction with the accompanying claims and drawings.

DETAILED DESCRIPTION OF THE INVENTION

Figure 1:
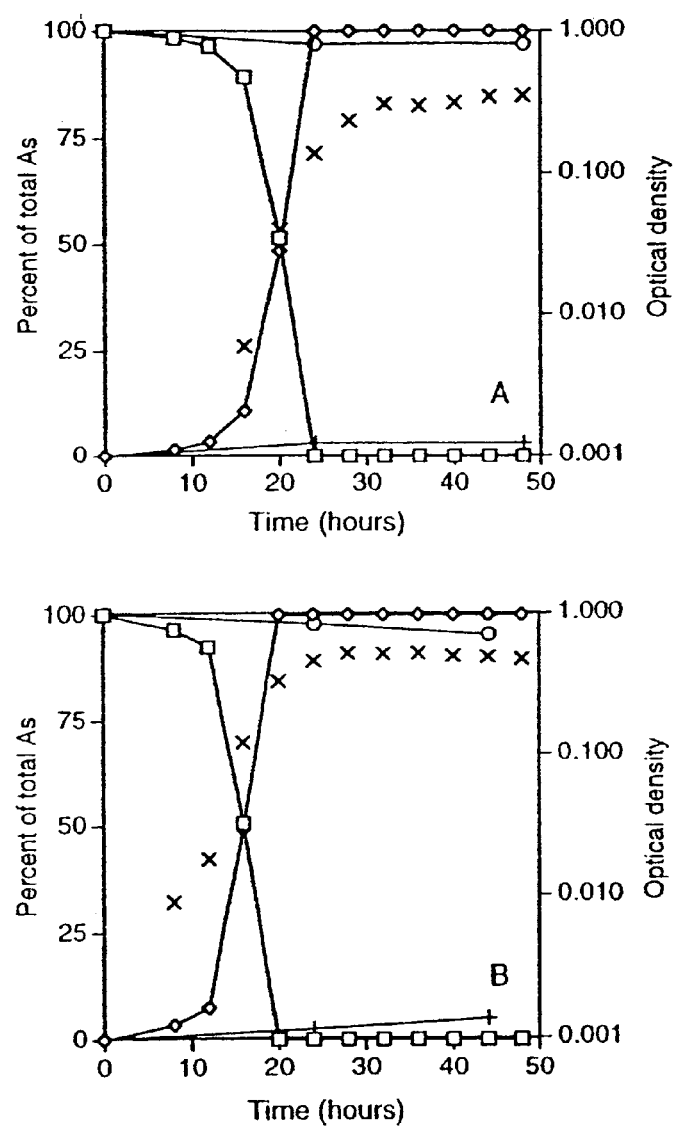
FIG. 1 shows arsenic speciation and culture density during arsenite oxidation by *Thermus aquaticus* YT1 (A) and *Thermus thermophilus* HB8 (B).

This invention is based on the finding that bacteria of the genus Thermus have the native ability to oxidize forms of arsenic to render them more susceptible to removal. The data presented below shows that three different bacterial strains from two different species of the Thermus genus, *Thermus aquaticus* YT 1, *Thermus aquaticus* HR-13 and *Thermus thermophilus* HB8, oxidize the more toxic and more mobile form of arsenic, arsenite, to the less toxic and less mobile arsenate. Thus, these exemplary bacteria may be used directly to detoxify arsenic. All three strains from the Thermus genus tested so far were effective in oxidizing arsenite. It is expected that other strains of the Thermus genus also have such activity.

The examples described below show that the arsenite oxidization efficiency of the Thermus species was reduced when their growth of the bacterial culture was inhibited. Thus, it is preferable to use a Thermus species for arsenic detoxification under conditions and at a temperature that favors the growth of the bacteria. Generally speaking, the growth temperature range of Thermus species is higher than other bacteria. This can be an advantage of the present invention in that it allows efficient arsenic detoxification even if the target's temperature is relatively high. One of ordinary skill in the art either knows or can easily determine the growth temperature range of a Thermus species. For example, it is known that the growth range of *Thermus aquaticus* is from 40 to 79 degrees Celsius and the growth range for *Thermus thermophilus* is from 47 to 85 degrees Celsius. It is also contemplated that the bacteria can be subject to mutation and selection to lower the optimal growth temperature, or change other preferred culture conditions, to permit use of the bacteria in lower temperature processes.

Thermus species can be used to detoxify arsenic in any source that can support survival or preferably growth of Thermus species. If the source can not by itself support survival or growth of a Thermus species, the source may be mixed with a medium that can support such in order to detoxify the source. Examples of an arsenic source that needs to be detoxified include but are not limited to a water source or soil that is contaminated by arsenite.

Thermus species can be used to detoxify arsenite in situ when the in situ conditions support Thermus species' survival or preferably support their growth. For example, in a geothermal electrical plant, the spent fluid after it has been extracted and used to run the turbines may contain high levels of arsenic. Thermus species can be used to oxidize arsenite in the spent fluid in situ because the spent fluid's temperature is high enough to support Thermus species' growth. Otherwise, in order to detoxify a contaminated source, the source has to be brought into a treatment facility so that it can be heated up to a temperature that supports Thermus species' growth.

The present invention can also be used to reduce arsenic concentration in a source when combined with an arsenate adsorption method. Other people have developed methods to reduce arsenic level in a source by arsenate adsorption. Examples of such methods include U.S. Pat. Nos. 6,203,709 and 5,591,346, which are hereby incorporated by reference in their entirety. When the present invention is combined with an arsenate adsorption method, both detoxification and arsenic concentration reduction can be achieved. It is known that arsenate can be adsorbed to a substrate such as iron oxyhydroxides and many other mineral species better than arsenite. Bhumbla, D. K., Keefer, R. F. In *Arsenic in the Environment, Part I: Cycling and Characterization*, Nriagu, J. O. Ed., John Wiley: New York, 1994, Chapter 3. It is preferable to combine the present invention with an adsorption substrate that has a higher affinity for arsenate than arsenite.

EXAMPLES

Materials and Methods

1. Laboratory experiments.

Bacterial strains and growth conditions. The strains *Thermus aquaticus* YT1 (DSM 625) and *Thermus thermophilus* HB8 (DSM 579) were purchased from the German Collection of Microorganisms and Cell Cultures. *Thermus aquaticus* HR-13 was collected from a hot spring in northern California containing 0.12 mM arsenite. Growth medium contained 0.2% (w/v) yeast extract, 0.8 g $L^{-1}$ $(NH_4)_2SO_4$, 0.4 g $L^{-1}$ $KH_2PO_4$, 0.18 g $L^{-1}$ $MgSO_4*7H_2O$, and 1.75 g $L^{-1}$ NaCl adjusted to pH 7.5 at room temperature with NaOH and autoclaved. When required, 2× (double the concentration of constituents) growth medium was diluted to 1× with autoclaved de-ionized water and a stock of filter-sterilized 3750 mg $L^{-1}$ arsenite (as arsenious acid; LabChem Inc.) adjusted to pH 7.5 with NaOH. Cultures of *T. aquaticus* and *T. thermophilus* were maintained in the presence of 75 mg $L^{-1}$ arsenite and washed twice with fresh growth medium prior to subsequent culture inoculations. All culturing was carried out using tightly-sealed 125 mL screw-cap polycarbonate flasks to prevent evaporation.

Arsenite oxidation assay. To test for the ability to oxidize arsenite, *T. aquaticus* and *T. thermophilus* were inoculated into 60 mL of growth medium containing 75 mg $L^{-1}$ arsenite and incubated at 70° C. with 125 RPM shaking. Experiments using uninoculated, sterile media with 75 mg $L^{-1}$ arsenite were also incubated under the same conditions. One-mL samples from biological and abiotic experiments were taken over time for measurements of cell density and for determinations of arsenic speciation. Optical density was measured at 600 nm using a Perkin Elmer Lambda 3 UV/VIS spectrophotometer. Samples were centrifuged and the supernatants decanted. Samples were then acidified by adding the concentrated trace metal-grade HCl to 1% (v/v) and stored at 4° C. for less than 7 days prior to arsenic analyses.

Measurements of arsenic speciation in laboratory experiments followed the protocol of Howard and Hunt. Howard, A. G., Hunt, L. E. *Anal. Chem.* 1993, 65, 2995–2998. Arsenic species were chromatographically separated using a 53 mm×7 mm Alltech adsorbosphere reversed-phase C-18 Rocket Column (part number 50625). Isocratic elution was performed using a mobile phase consisting of 5.0 mM tetrabutylammonium hydroxide in $H_2O$:methanol (95:5; v/v) adjusted to pH 7.0 with $H_3PO_4$. An injection volume of 20 μL and flow rate of 2.5 mL $min^{-1}$ were used. After separation of As(III) and As(V), the post-column flow was routed to a Cetac HGX-100 hydride generator where 6 M HCl and sodium borohydride solution (1% (w/v) $NaBH_4$, 0.5% NaOH (v/v), 0.3% (v/v) Antifoam A (Sigma); made fresh daily and filtered) were added, generating arsine ($AsH_3$). This mixture was pumped into a gas-liquid separator and the arsine was flushed with nitrogen gas (400 mL $min^{-1}$) to a flame-heated silica T-tube. The atomic absorption was detected at 193.7 nm using a Unicam 969 flame atomic absorption spectrometer.

2. Field Studies.

Sample Collection. Fieldwork was carried out over a two-day period in September 2000 at the Twin Butte Vista Hot Spring in the Lower Geyser Basin of Yellowstone National Park. Five sampling stations were designated at intervals along the main overflow channel spanning an approximately 18.5 meter distance. Biological samples were collected using sterile forceps, placed in 15 ml screw-cap Falcon tubes containing 4% (w/v) paraformaldehyde in phosphate-buffered saline (PBS; 8.0 g $L^{-1}$ NaCl, 0.2 g $L^{-1}$ KCl, 1.44 g $L^{-1}$ $Na_2HPO_4*7H_2O$, 0.24 g $L^{-1}$ $KH_2PO_4$, pH 7.2), and kept on ice. Within 8 hours of collection, samples were centrifuged, washed once with cold PBS, and resuspended in ethanol:PBS (1:1; v/v). Fixed biological samples were kept on ice during transport and stored at −20° C. in the laboratory.

Three sets of water samples were collected by syringe from each station and were filtered (0.2 μm Pall Acrodisc) into high-density polyethylene screw-cap bottles. Samples for As and Fe speciation determinations were acidified by 1% (v/v) additions of concentrated trace metal-grade HCl. Samples for cations measurements were acidified by 1% (v/v) additions of electronic-grade $HNO_3$. The final set of water samples were left unacidified for anion analysis.

Laboratory determinations of inorganic constituents. All reagents were of purity at least equal to the reagent-grade standards of the American Chemical Society. Doubly-distilled de-ionized water and re-distilled acids were used in all preparations. USGS standard reference water samples were used as independent standards. Samples were diluted as necessary to bring the analyte concentration within the optimal range of the method. For elemental analyses, several dilutions of each sample were analyzed to check for concentration effects on the analytical method. Spike recoveries were also performed on several samples.

Concentrations of major cations and trace metals were determined using a Leeman Labs—DRE inductively-coupled plasma optical-emission spectrometer. Major cations were analyzed using the radial view while the axial view was used for trace metals. As (III/V) redox species were determined using a flow injection analysis system for the generation of arsine and detection using atomic absorption spectrometry (Perkin Elmer—Analyst 300). McCleskey, R. B., Nordstrom, D. K., and Ball, J. W. In *U.S. Geological Survey Workshop on Arsenic in the Environment, Denver*, CO, Feb. 21–22, 2000. Fe(II/III) redox species were determined using a modification of the FerroZine colorimetric method. Stookey, L. L. *Anal. Chem.* 1970, 42, 779–781. Concentrations of major anions were determined chromatographically, Brinton, T. I., Antweiler, R. C., Taylor, H. E. *US. Geological Survey, Open-File Report*95-426A, 1995, using a Dionex 2010i ion chromatograph with 10-$\mu$L and 50-$\mu$L sample loops. Alkalinity (as $HCO_3^-$) was determined using an Orion 960 autotitrator and standardized $H_2SO_4$. Barringer, J. L., Johnsson, P. A., *US. Georlogical Survey, Water Resources Investigations Report* 89–4029, 1989. Specific conductance was measured using an Orion conductivity meter (model 126).

Field geochemical analyses. Measurements of pH, Eh, and water temperature were made in the field using an Orion 290A portable meter and Orion 9107 pH/temperature and Orion 9678 redox electrodes. The pH electrode was calibrated with pH 4, 7 and 10 standard buffers (Fisher) heated to sample temperature by immersion of the buffer vials in the hot spring waters where sampling was performed. Preparation of the ZoBell's solution to calibrate the platinum electrode for Eh measurements and the values for the standard half-cell potentials used in calculating sample Eh are after the method in Nordstrom and White. Nordstrom, D. K., White, F. D. In *US. Geological Survey Techniques of Water Resources Investigations Book* 9, Wilde, F. D., Radtke, D. B. Eds; 1998, Chapter A6. The Zobell's solution was prepared immediately prior to use and brought to sample temperature by immersion of the sealed solution vial in the hot spring fluids before calibration of the meter. Sulfide was measured colorimetrically in the field using a Hach DR/2010 portable datalogging spectrophotometer after Hach method #690.

Fluorescence in-situ hybridizations (FISH). The 16S rRNA-targeted oligonucleotide probes Eub338, Arch915, S-G-Thus-0438-a-A-18, Taq1258, and Tth1258 were used in this study. Amann, R. I., Binder, B. J., Olson, R. J., Chislholm, S. W., Devereux, R., Stahl, D. A. *Appl. Environ. Microbiol.* 1990, 56, 1919–1925; Stahl, D. A., Amann, R. in *Nucleic acid techniques in bacterial systematics*, Stackebrant, E., Goodfellow, M. Eds., John Wiley: Chichester, UK, 1991, pp. 205–248; Harmsen, H. J. M., Prieur, D., Jeanthon, C. *Appl. Environ, Microbiol.* 1997, 63, 4061–4068; Byers, H. K., Patel, B., Stackebrandt, E. *System. Appl. Microbiol.* 1997, 20, 248–254. Probes were synthesized and labeled with fluorescein (Eub338 and Arch915) or Cy3 (Thus0438, Taq 1258, and Tth 1258) by the University of Wisconsin Biotechnology Center.

Hybridizations were performed according to the protocol of Bond et al. Bond, P. L., Banfield, J. F. *Microb. Ecol.* 2001, in press. Fixed environmental samples were homogenized by rigorous vortexing and spotted to gelatin-coated multi-well slides. The organisms *Thermus aquaticus* YT1, *Thermus thermophilus* HB8, *Pseudomonas putida*, *Thermoplasma acidiphilum*, and *Sulfolobus sulfataricus* were fixed and used as controls during the hybridizations. The hybridization buffer contained 20% formamide and each well was probed with Arch915 and Eub338, plus either Thus0438, Taq1258, or Tth1258.

Samples were examined using a Leica LEITZ DMRX epifluorescence microscope equipped with Chroma Technology filter sets 41007a for detection of Cy3 and 41001 for detection of fluorescein. The percentages of hybridized cells were quantified by comparing the total number of cells in a field of view labeled with the Arch915 and Eub338 probes relative to the number of cells labeled with either the Thus0438, Taq1258, or Tth1258 probes. For stations 2–5, a minimum of 3,000 cells in at least 6 separate wells were counted for each sample. 697 cells in 4 separate wells were counted for station 1. The sample in FIG. 5 was stained with DAPI (4', 6',-diamidino-2-phenylindole) and the image was captured using a Hamamatsu digital CCD camera (C4742-95) with AxioVision 2.0.5 software (Zeiss, N.Y., USA).

Results

1. Culturing Experiments.

Laboratory experiments conducted to examine *Thermus aquaticus* YT1 for the ability to oxidize arsenite to arsenate showed that within 12 hours after inoculation, arsenite oxidation was accelerated relative to abiotic controls (FIG. 1A: Arithmetic plot: ▫, arsenite; ◊, arsenate; o, arsenite-abiotic control; †, arsenate-abiotic control. Logarithmic plot: X, optical density of culture). A lag period of slow oxidation during the first 16 hours of incubation was followed by rapid arsenite oxidation coinciding with the exponential phase of growth. Within 24 hours, 100 percent of arsenite was oxidized to arsenate by *T. aquaticus* YT1 at a rate of 0. 139 mg $L^{-1}$ $min^-$ during exponential growth. *Thermus thermophilus* HB8 showed similar results (FIG. 1B: arithmetic plot: ▫, arsenite; ◊, arsenate; o, arsenite-abiotic control; †, arsenate-abiotic control; logarithmic plot: X, optical density of culture). *Thermus thermophilus* HB8 oxidized arsenite at a rate of 0.144 mg $L^{-1}$ $min^{-1}$ during exponential growth. In each of the abiotic control experiments, only about 5 percent of the arsenite was oxidized after 48 hours (FIG. 1) at an average rate of 0.001 mg $L^{-1}$ $min^{-1}$ (n=3; standard deviation=0.00036). Experiments carried out with *Thermus aquaticus* HR13 showed similar results to those with *Thermus aquaticus* YT1 and *Thermus thermophilus* HB8 described above.

Figure 2:
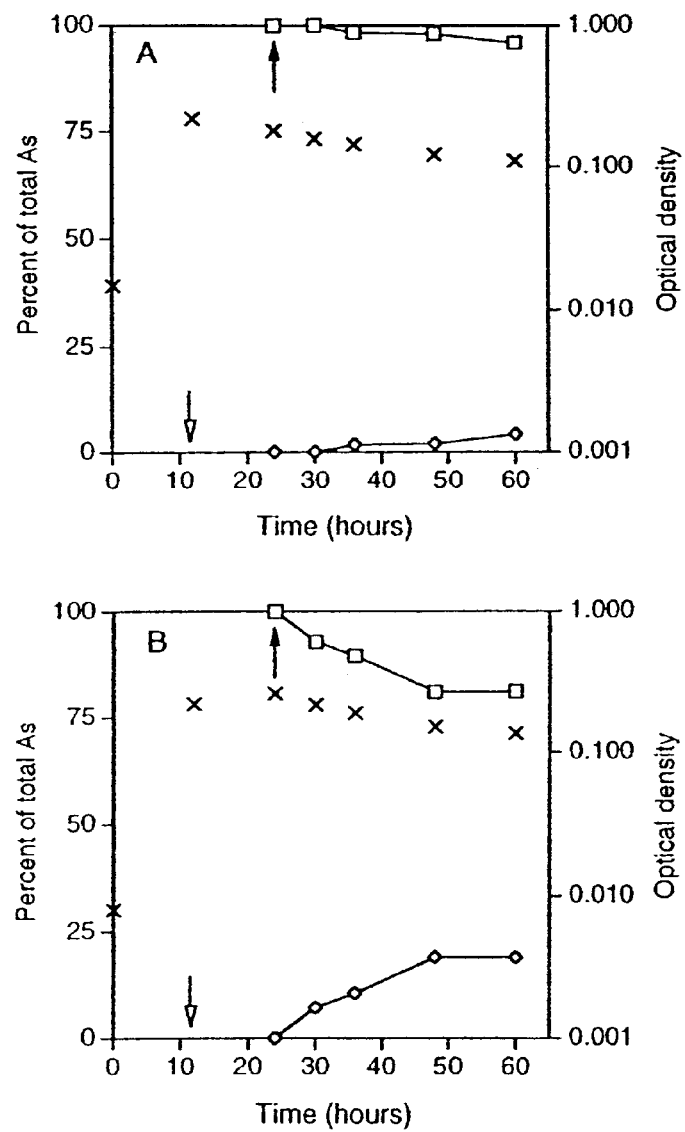
FIG. 2 shows arsenic speciation and culture density during antibiotic-inhibited culturing of *Thermus aquaticus* YT1 (A) and *Thermus thermophilus* HB8 (B).

To confirm arsenite was oxidized through the metabolic activity of *T. aquaticus* YT1 and *T. thermophilus* HB8, culturing experiments were carried out in which growth was inhibited by antibiotics (FIG. 2: open arrows indicate the addition of 2.0 mg $L^{-1}$ kanamycin and 2.0 mg $L^{-1}$ ampicillin; filled arrows indicate the addition of 75 mg $L^{-1}$ As(III); arithmetic plot: ▫, arsenite; ◊, arsenate; logarithmic plot: X, optical density of culture). The rate of arsenic oxidation by antibiotic-treated cells was significantly reduced relative to untreated cells. Experiments carried out with *Thermus aquaticus* HR13 showed similar results.

Additional experiments were conducted to ascertain whether *T. aquaticus* and *T. thermophilus* are capable of chemolithoautotrophic growth by arsenite oxidation. Using low levels of yeast extract (0.020, 0.002, and 0.000%; w/v) as a carbon source, cultures were incubated with and without arsenite present. Growth in these experiments was extremely slow and cultures grown with arsenite showed no change in their growth rate compared to cultures grown in the absence of arsenite.

2. Field Investigations.

Physical and geochemical parameters. The Twin Butte Vista Hot Spring is comprised of a small pool with a vent at the western edge and overflow waters draining in 3 channels. The flow rate in the 2 western channels was irregular, increasing with sporadic surges from the vent, and samples from these drainages were not used in this study. Waters overflowed via the northern channel at a nearly constant rate, buffered by the deep pool between the vent and outlet. The north drainage channel was very well confined and the residence time for waters in the sampled region (flow from station 1 to 5) was estimated to be approximately 2 minutes.

Geothermal waters venting the Twin Butte Vista Hot Spring were alkaline, with an average pH of 8.8 throughout the north drainage channel (Table 1). Water temperatures decreased from 82.6 to 65.1° C. during flow from station 1 to 5. Conditions were reducing at the pool, becoming more oxidizing with distance as Eh increased from −87.2 mV at station 1 to 3.3 mV at station 5. Sulfide concentrations fell from 0.13 to 0.017 mg $L^{-1}$ as sulfate remained nearly constant between the first and final sampling stations. Results of additional chemical analyses are shown in Table 1.

The total dissolved arsenic concentration was approximately constant at 2.5 mg $L^{-1}$ throughout the north drainage channel (Table 2). While total As behaved conservatively, specification changed dramatically as waters flowed downstream. As(III) was highest at the first sampling station at 1.9 mg $L^{-1}$ and decreased at each subsequent station to 0.61 mg $L^{-1}$ at the final point. Correspondingly, As(V) was low near the pool at 0.6 mg $L^{-1}$ and increased with distance to 1.9 mg $L^{-1}$ at the final sampling station. The rate of arsenite oxidation between stations 1 and 5 was estimated to be approximately 0.5 mg $L^{-1}$ min$^{-1}$.

Laboratory experiments were performed to test for catalysis of As(III) oxidation by mineral surfaces. Sediments collected from the north drainage channel near station 1 (150 mg) were autoclaved and placed in a flask with 10 mL of filter-sterilized fluids collected from the same location. A spike of 75 mg $L^{-1}$ As(III) was added to the flask which was then incubated for 48 hours at 70° C. with 125 RPM shaking. The rate of arsenite oxidation in this experiment was linear at 0.002 mg $L^{-1}$ min$^{-1}$.

Microbial characterizations. Pale-orange biofilms were visible beginning at ~2 m downstream of station 1 and were evident in the remainder of the channel. These microbial streamers, attached to sediments and other surfaces, were often very dense and formed thick filaments up to 10 cm long. Microscopic observations revealed a very low cell density at station 1 consisting primarily of cocci. Stations 2 and 3 were dominated by dense, homogenous masses of thin filamentous rods. Samples from stations 4 and 5 also contained large accumulations of thin filamentous rods in addition to clusters of thick green rods (likely cyanobacteria).

Figure 3:
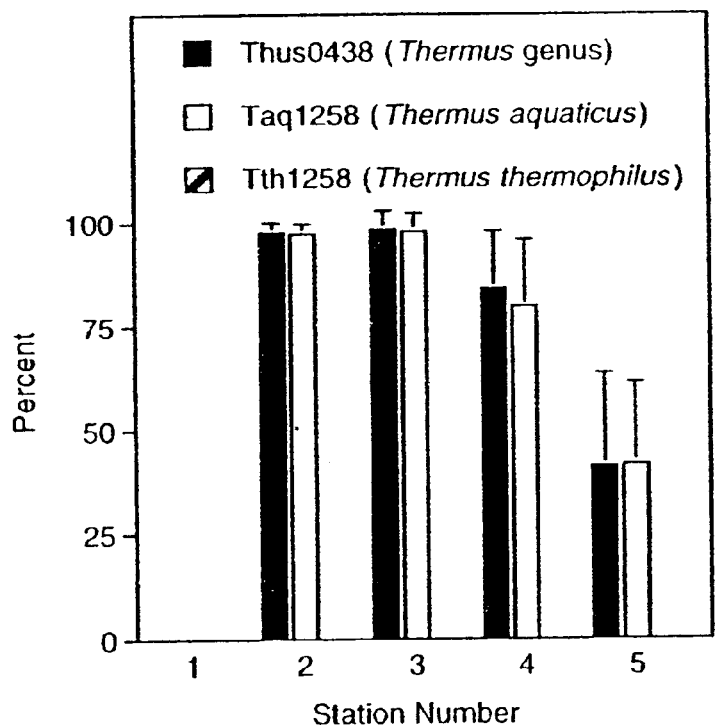
FIG. 3 shows quantification of the genus Thermus and the species *Thermus aquaticus* and *Thermus thermophilus* at each station, as determined by FISH.

To label individual cells and quantify their relative proportion of the microbial community at each station, fluorescence in-situ hybridizations were performed. Results of FISH analyses are shown in FIG. 3 (values are expressed as the percent of (Arch915+Eub338) hybridized cells; error bars represent one standard deviation; only the positive portions of error bars are shown). The probes Arch915 and Eub338, specific for the archaeal and bacterial domains respectively, were used to label all viable prokaryotic cells. Thus0438, specific at the genus level, was used to detect Thermus species. The species-specific probes Taq1258 and Tth1258 were used to identify and enumerate *Thermus aquaticus* and *Thermus thermophilus* respectively.

At station 1, no cells were detected with the genus- or species-specific probes, indicating that Thermus species were not present in the pool. As the hot springs waters cooled with distance, *Thermus aquaticus* was found to be colonizing the drainage channel at stations 2 and 3, occurring as nearly 100% of the microbial population. Stations 4 and 5 contained a lower percentage of *Thermus aquaticus* (80 and 42% respectively), although the species remained prominent. *Thermus thermophilus* was not detected in any of the drainage samples.

TABLE 1

Physical and Chemical Characteristics of the Twin Butte Vista Hot Spring North Drainage Channel.

| Station Number | Field Blank[b] | 1 | 2 | 3 | 4 | 5 |
|---|---|---|---|---|---|---|
| Approx. Distance to pool (m) | — | 0 | 3.8 | 6 | 13.5 | 18.5 |
| Temperature (° C.) | — | 82.6 | 79.0 | 77.7 | 72.6 | 65.1 |
| pH | — | 8.7 | 8.7 | 8.7 | 8.8 | 8.9 |
| Eh (mV) | — | −87.2 | −76.6 | −36.8 | −62.1 | 3.3 |
| Conductance (uS/cm) | — | 1449 | 1460 | 1471 | 1479 | 1497 |
| Al[a] | <0.08 | 0.26 | 0.28 | 0.3 | 0.33 | 0.33 |
| B | <0.003 | 3.2 | 3.2 | 3.2 | 3.1 | 3.2 |
| Ba | <0.0005 | <0.0005 | <0.0005 | <0.0005 | <0.0005 | <0.0005 |
| Be | <0.0001 | <0.0001 | 0.0004 | 0.001 | 0.002 | 0.002 |
| Ca | <0.05 | 0.22 | 0.24 | 0.35 | 0.46 | 0.46 |
| Cd | <0.001 | <0.001 | <0.001 | <0.001 | <0.001 | <0.001 |
| Co | <0.001 | <0.001 | <0.001 | <0.001 | <0.001 | <0.001 |
| Cr | <0.002 | <0.002 | <0.002 | <0.002 | 0.002 | 0.002 |
| Cu | <0.001 | <0.001 | <0.001 | <0.001 | <0.001 | <0.001 |
| K | 0.012 | 12 | 12 | 12 | 13 | 13 |
| Li | <0.008 | 3.2 | 3.5 | 3.5 | 3.6 | 3.7 |
| Mg | <0.06 | <0.0001 | <0.0001 | <0.0001 | 0.001 | 0.001 |
| Mn | <0.001 | <0.001 | <0.001 | 0.001 | 0.002 | 0.002 |
| Na | <0.04 | 320 | 310 | 310 | 330 | 340 |
| Ni | <0.002 | <0.002 | <0.002 | <0.002 | <0.002 | <0.002 |
| Pb | <0.006 | <0.006 | <0.006 | <0.006 | <0.006 | 0.006 |
| $SiO_2$ | <0.01 | 190 | 270 | 240 | 170 | 190 |
| Se | <0.04 | <0.04 | <0.04 | <0.04 | <0.04 | <0.04 |
| Sr | <0.001 | <0.001 | <0.001 | <0.001 | <0.001 | <0.001 |
| V | <0.001 | <0.001 | <0.001 | <0.001 | <0.001 | <0.001 |
| Zn | <0.001 | <0.001 | <0.001 | <0.001 | <0.002 | 0.001 |
| Fe (Total) | 0.004 | 0.046 | 0.016 | 0.015 | 0.014 | 0.002 |
| Fe (II) | — | 0.021 | 0.009 | 0.006 | 0.002 | <0.002 |
| F | <0.05 | 21 | 22 | 21 | 21 | 22 |
| Cl | <0.4 | 280 | 280 | 280 | 280 | 280 |
| Br | <0.1 | 0.99 | 0.86 | 0.94 | 0.97 | 0.96 |
| $NO_3$ | <0.5 | <0.5 | <0.5 | <0.5 | <0.5 | <0.5 |
| $SO_4$ | <0.8 | 16 | 16 | 16 | 16 | 17 |
| $S^{2-}$ | — | 0.13 | 0.13 | 0.10 | 0.04 | 0.017 |
| Alkalinity (as $HCO_3$) | — | 337 | 341 | 345 | 347 | 355 |

TABLE 2

Arsenic Measurements for the North Drainage channel of the Twin Butte Vista Hot Spring.

| Sample | As (Total)$^a$, mgL$^{-1}$ | | | As (III)$^a$, mg L$^{-1}$ | | | As (V), mg L$^{-1}$ |
|---|---|---|---|---|---|---|---|
| | n | mean | ± | n | mean | ± | by difference |
| Field Blank$^b$ | 3 | <0.0001 | | 2 | <0.0002 | | |
| Station 1 | 2 | 2.5 | 0.01 | 3 | 1.9 | 0.04 | 0.6 |
| Station 2 | 2 | 2.5 | 0.02 | 3 | 1.7 | 0.05 | 0.8 |
| Station 3 | 2 | 2.5 | 0.02 | 3 | 1.3 | 0.02 | 1.2 |
| Station 4 | 2 | 2.5 | 0.00 | 3 | 1.0 | 0.04 | 1.5 |
| Station 5 | 2 | 2.5 | 2.02 | 3 | 0.61 | 0.03 | 1.9 |

We claim:

1. A method for converting arsenite to arsenate, comprising the step of:
   incubating bacteria of a Thermus species in a source containing arsenite at a temperature at which the bacteria can convert at least some of the arsenite to arsenate.

2. The method of claim 1, wherein the temperature is between about 40 degrees Celsius and about 85 degrees Celsius.

3. The method of claim 1, wherein the Thermus species is *Thermus aquaticus*.

4. The method of claim 3, wherein the temperature is between about 40 degrees Celsius and about 79 degrees Celsius.

5. The method of claim 3, wherein the *Thermus aquaticus* is *Thermus aquaticus* YT-1.

6. The method of claim 1, wherein the Thermus species is *Thermus thermophilus*.

7. The method of claim 6, wherein the temperature is between about 47 degrees Celsius and about 85 degrees Celsius.

8. The method of claim 6, wherein the *Thermus thermophilus* is *Thermus thermophilus* HB8.

9. The method of claim 1, wherein the source containing arsenite is water.

10. The method of claim 1, wherein the source containing arsenite is soil.

11. A method for converting arsenite to arsenate, comprising the steps of:
   screening for a Thermus species that can convert arsenite to arsenate comprising the steps of:
   incubating bacteria of a Thermus species in a source containing arsenite at a temperature at which the species grows; and
   determining whether the species can convert arsenite to arsenate;
   selecting the species if it can convert arsenite to arsenate;
   incubating the Thermus species selected from above in a source containing arsenite at a temperature at which the species can convert at least some of the arsenite to arsenate.

* * * * *